United States Patent
Liu

(10) Patent No.: US 9,157,830 B2
(45) Date of Patent: Oct. 13, 2015

(54) DROP TEST APPARATUS

(71) Applicants: HONG FU JIN PRECISION INDUSTRY (ShenZhen) CO., LTD., Shenzhen (CN); HON HAI PRECISION INDUSTRY CO., LTD., New Taipei (TW)

(72) Inventor: Fu-Ming Liu, Shenzhen (CN)

(73) Assignees: HONG FU JIN PRECISION (ShenZhen) CO., LTD., Shenzhen (CN); HON HAI PRECISION INDUSTRY CO., LTD., New Taipei (TW)

( * ) Notice: Subject to any disclaimer, the term of this patent is extended or adjusted under 35 U.S.C. 154(b) by 222 days.

(21) Appl. No.: 14/015,733

(22) Filed: Aug. 30, 2013

(65) Prior Publication Data

US 2014/0182355 A1    Jul. 3, 2014

(30) Foreign Application Priority Data

Dec. 28, 2012    (CN) .......................... 2012 1 0583441

(51) Int. Cl.
  *G01N 3/00* (2006.01)
  *G01M 7/08* (2006.01)
  *G01N 3/303* (2006.01)

(52) U.S. Cl.
  CPC . *G01M 7/08* (2013.01); *G01N 3/303* (2013.01)

(58) Field of Classification Search
  CPC ............. G01M 7/08; B64G 7/00; F42B 35/00
  USPC ...................... 73/12.06, 12.04, 79, 12.01, 167
  See application file for complete search history.

(56) References Cited

U.S. PATENT DOCUMENTS

| | | |
|---|---|---|
| 2010/0162789 A1* | 7/2010 | Su ................................ 73/12.06 |
| 2012/0024040 A1* | 2/2012 | Le et al. ....................... 73/12.06 |
| 2012/0227464 A1* | 9/2012 | Yu et al. ....................... 73/12.06 |

* cited by examiner

*Primary Examiner* — Lisa Caputo
*Assistant Examiner* — Nigel Plumb
(74) *Attorney, Agent, or Firm* — Novak Druce Connolly Bove + Quigg LLP

(57) ABSTRACT

A drop test apparatus includes a frame, a first blocking board, a second blocking board, two first pivot poles and two second pivot poles. The frame includes a base board and a holding board above the base board for holding a tested product. The first blocking board is located between the base board and the holding board for placing the tested product when the tested product is dropped from the holding board. The second blocking board is secured to the base board. The two first pivot holes and the second two pivot poles are connected the first blocking board with the second blocking board, and a distance between the first blocking board and the second support is adjusted.

20 Claims, 5 Drawing Sheets

DROP TEST APPARATUS

BACKGROUND

1. Technical Field

The present disclosure relates to testing apparatuses, and more particularly to a drop test apparatus for a product.

2. Description of Related Art

In a drop test for a product, the product is usually placed on a holding board, and a blocking board is provided to support the tested product when the tested product is dropped. Usually, a distance between the holding board and the blocking board is constant. Therefore, there is room for improvement in the art.

BRIEF DESCRIPTION OF THE DRAWINGS

Many aspects of the embodiments can be better understood with references to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
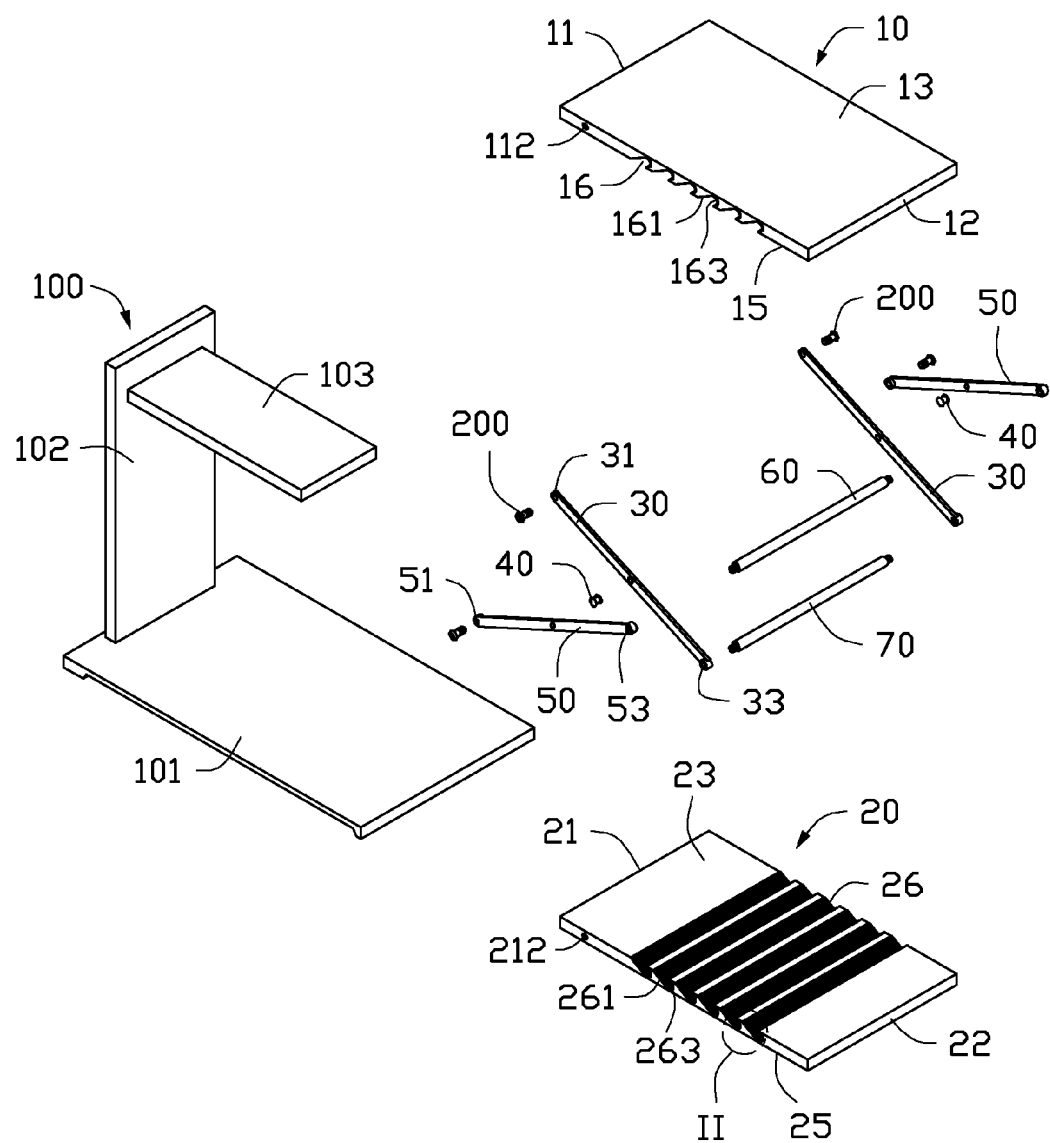
FIG. 1 is an exploded, isometric view of a drop test apparatus in accordance with an embodiment.

FIG. 1 illustrates a drop test apparatus in accordance with an embodiment, which comprises a frame 100, a first blocking board 10, and a second blocking board 20.

The frame 100 comprises a base board 101, a support board 102, and a holding board 103. The support board 102 is secured to the base board 101, and the holding board 103 is secured to the support board 102 above the base board 101. The base board 101 is substantially parallel to the holding board 103, and the support board 102 is substantially perpendicular to the base board 101 and the holding board 103. The holding board 103 is configured to place a tested product.

Figure 2:
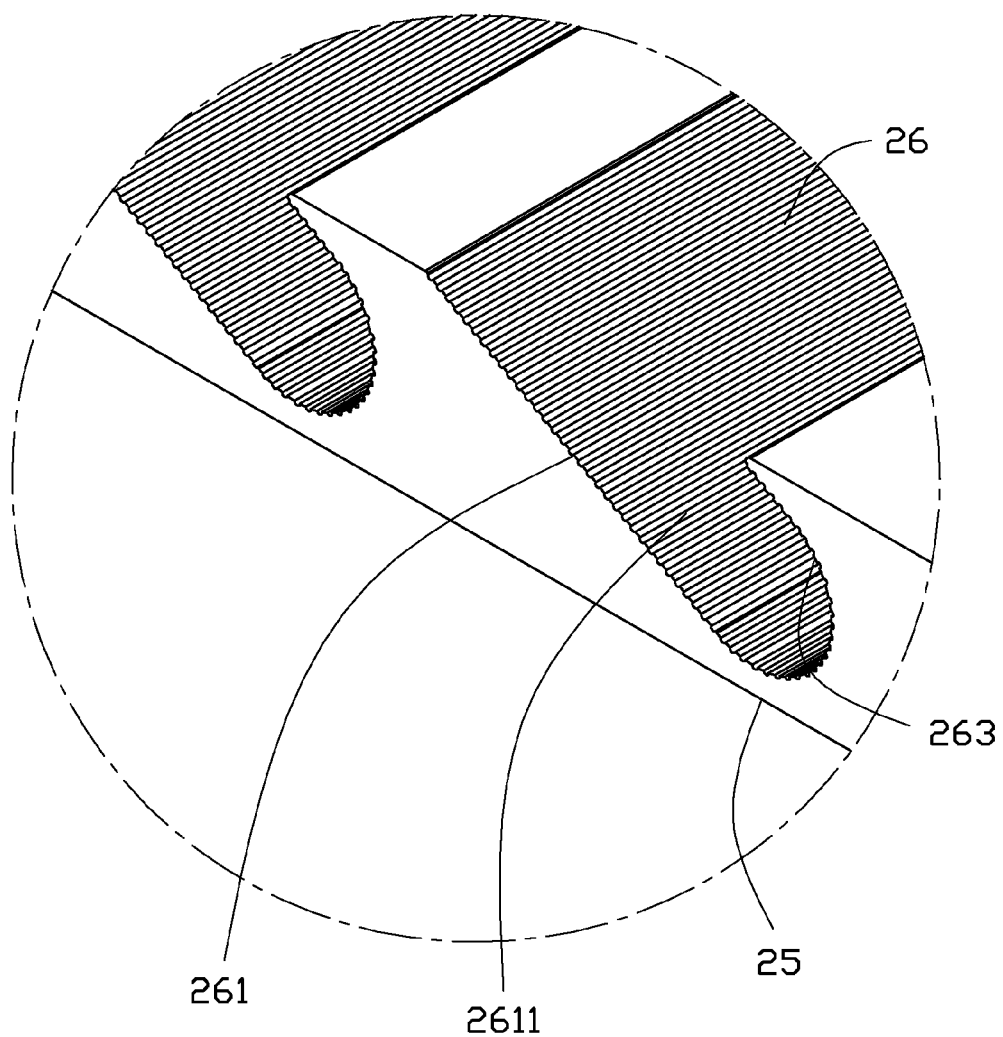
FIG. 2 is an enlarged viewed of a circled portion II of FIG. 1.

FIGS. 1 and 2 show that the first blocking board 10 comprises a first mounting end 11 and a second mounting end 12, opposite to the first mounting end 11. The first blocking board 10 defines two first pivot holes 112 in two opposite sides of the first mounting end 11. The first blocking board 10 further comprises a first top surface 13 and a first bottom surface 15, opposite to the first top surface 13. The first top surface 13 is configured to support the tested product drop from the holding board 103. The first bottom surface 15 defines a plurality of locking slots 16. Each of the plurality of locking slots 16 comprises a guiding surface 161 and a locking surface 163 extending from the guiding surface 161. The guiding surface 161 of each of the plurality of locking slots 16 is slanted relative to the first bottom surface 15, and a plurality of protrusions (not shown) protrude from the guiding surface 161. The locking surface 163 of each of the plurality of locking slots 16 may be an arc-shaped surface. In an embodiment, the locking surface 163 of each of the plurality of locking slots 16 is semicircular surface.

The second blocking board 20 comprises a first securing end 21 and a second securing end 22 opposite to the first securing end 21. The second blocking board 20 defines two second pivot holes 211 in opposite sides of the first securing end 21. The second blocking board 20 further comprises a first upper surface 23 and a first low surface 25, opposite to the first upper surface 23. The first upper surface 23 defines a plurality of latching slots 26. Each of the plurality of latching slots 26 comprises a directing surface 261 and a receiving surface 263 extending from the directing surface 261. The directing surface 261 of each of the latching slots 26 is slanted relative to the first upper surface 23, and a plurality of projections 2611 protrudes from the receiving surface 263. The receiving surface 263 of each of the plurality of latching slots 26 may be an arc-shaped surface. In the embodiment, the receiving surface 263 of each of the plurality of latching slots 26 is semicircular surface.

The drop test apparatus further comprises two first pivot poles 30, two second pivot poles 50, a first positioning shaft 60, and a second positioning shaft 70.

One end of each of the two first pivot poles 30 defines a first through hole 31, and a first mounting post 33 is located on an opposite end. A first installing hole (not labeled) is defined in a center of each of the two first pivot poles 30. One end of each of the two second pivot poles 50 defines a second through hole 51, and a second mounting post 53 is located on an opposite end. A second installing hole (not labeled) is defined in a center of each of the two second pivot poles 50.

In an embodiment, a cross section of each of the first positioning shaft 60 and the second positioning shaft 70 is circular. A diameter of the first positioning shaft 60 is equal to or slightly less than that of the first locking surface 163, and a diameter of the second positioning shaft 70 is equal to or slightly less than that of the receiving surface 263.

Figure 3:
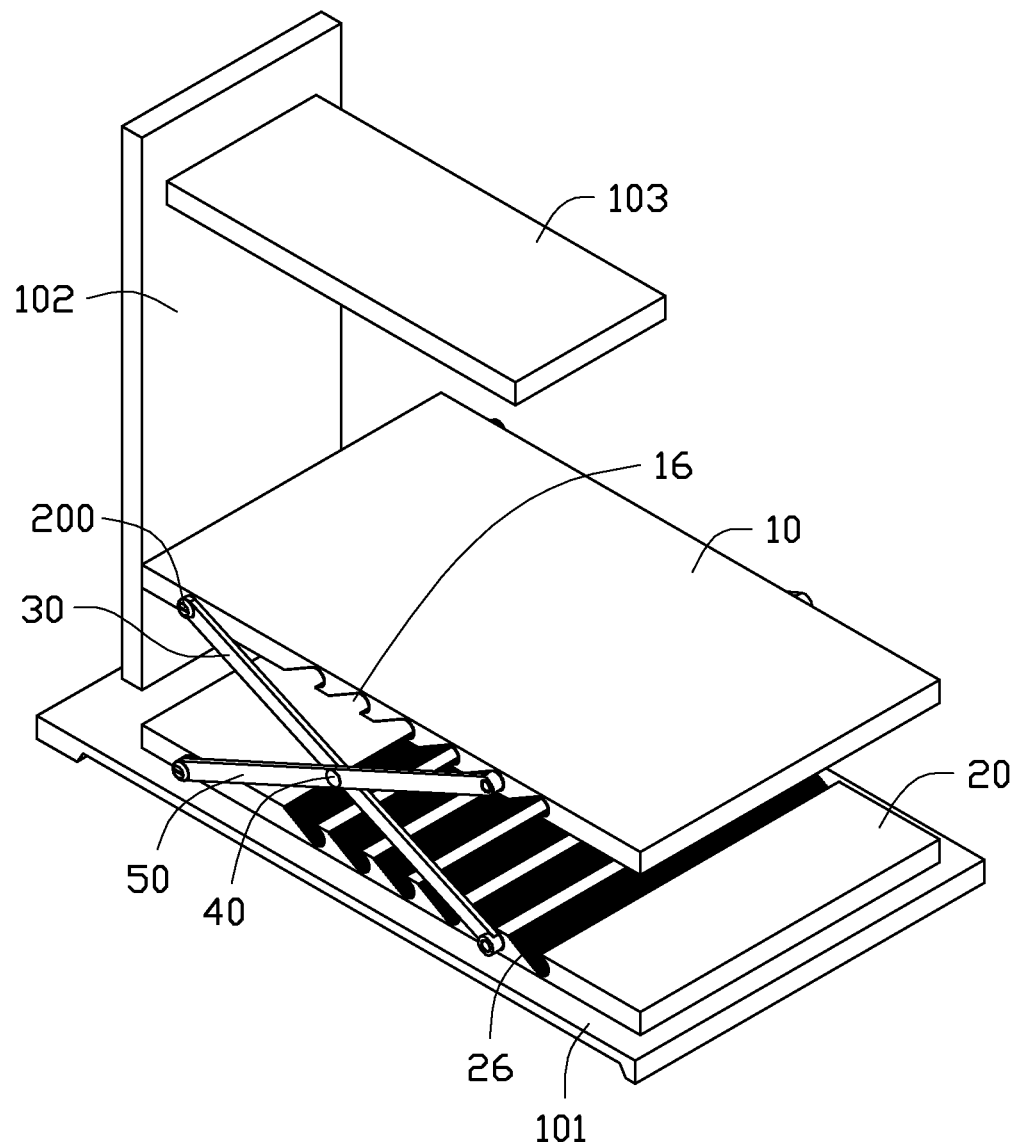
FIG. 3 is an isometric view of assembling the drop test apparatus of FIG. 1.
Figure 4:
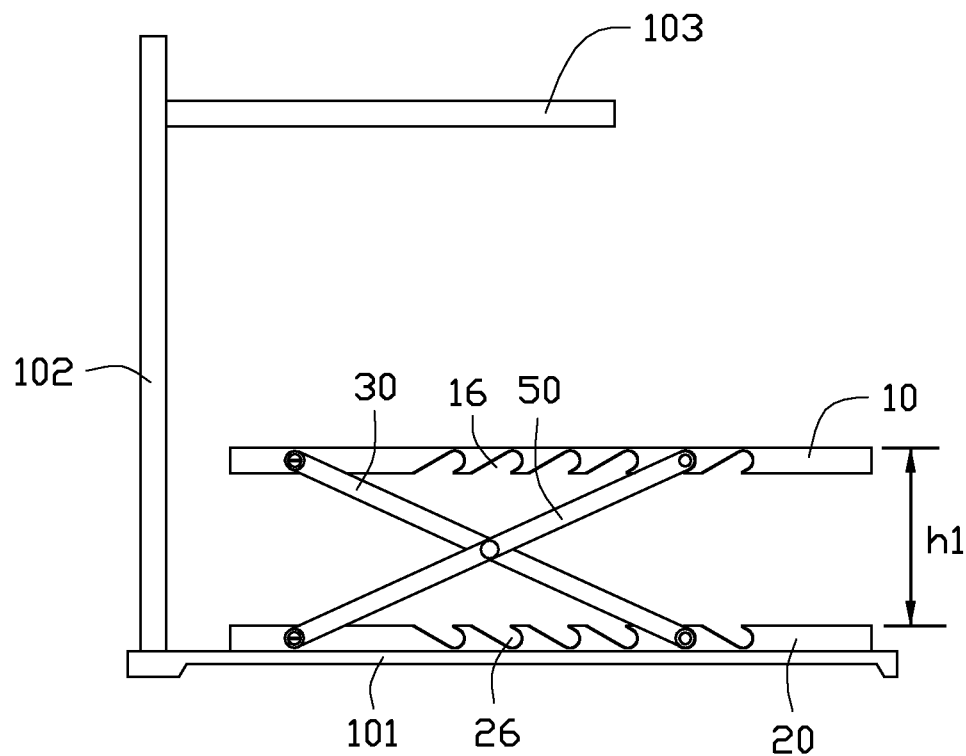
FIG. 4 is a side view of the drop test apparatus of FIG. 3 and shows a distance between a first blocking board and a second blocking board in h1.
Figure 5:
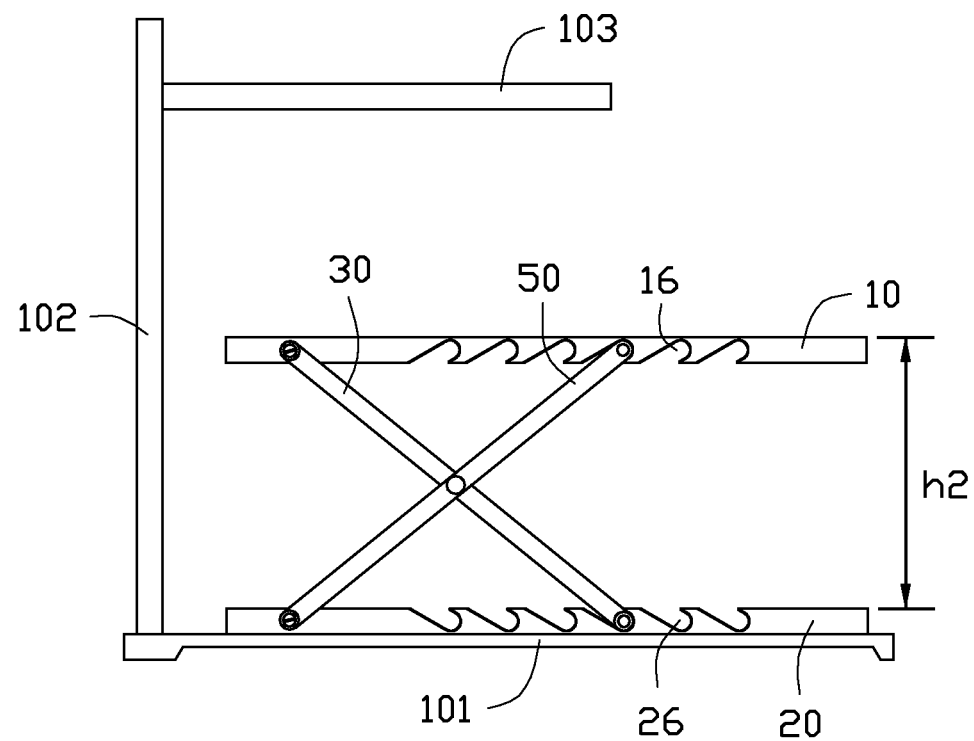
FIG. 5 is similar to FIG. 4, but shows a distance between the first blocking board and the second blocking board in h2.

FIGS. 3 to 5 show that in assembly, the second blocking board 20 is secured to the base board 101 by any known means, such as by screws. A fixing pin 40 extends into the first installing hole of each of the two first pivot poles 30 and the second installing hole of each of the two second pivot poles 50, to secure the two first pivot poles 30 to the two second pivot poles 50. Each of the two first pivot poles 30 is rotatable relative to each of the two second pivot poles 50 about the fixing pin 40. A fastener 200, such as screw, extends into the first through hole 31 of each of the two first pivot poles 30 and each of the two first pivot holes 112, to secure the two first pivot poles 30 to the first mounting end 11 of the first blocking board 10. Each of the two first pivot poles 30 is rotatable relative to the first blocking board 10 about the fastener 200. Another fastener 200 extends into the second through hole 51 and each of the two second pivot holes 211, to secure the two second pivot poles 50 to the first securing end 21 of the second blocking board 20. Each of the two second pivot poles 50 is rotatable relative to the second blocking board 20 about the another fastener 200. Two opposite ends of the first positioning shaft 60 are engaged with the two second mounting posts 53 of the two second pivot poles 50. Two opposite ends of the second positioning shaft 70 are engaged with the two first mounting posts 33 of the two first pivot poles 30. The first positioning shaft 60 is positioned in one of the plurality of locking slots 16 and abuts against the locking surface 163.

The second positioning shaft 70 is positioned in one of the plurality of latching slots 26 and abuts against the receiving surface 263. The first blocking board 10 is supported above the second blocking board 20 by the two first pivot poles 30, the two second pivot poles 50, the first positioning shaft 60, and the second positioning shaft 70. A distance h1 between the first blocking board 10 and the second blocking board 20 can be adjusted to change a distance between the holding board 103 and the first blocking board 10.

When the first distance h1 between the first blocking board 10 and the second blocking board 20 is adjusted, the first blocking board 10 is rotated up about the fastener 200. The first positioning shaft 60 moves out of the locking slot 16 from the locking surface 163 to the guiding surface 161, and the second positioning shaft 70 moves out of the latching slot 26 from the receiving surface 263 to the directing surface 261. The two first pivot poles 30 and the two second pivot poles 50 are rotated relative to the first blocking board 10 and the second blocking board 20, until the first positioning shaft 60 and the second positioning shaft 70 can be positioned on the directing surface 261 of another latching slot 26 and the guiding surface 161 of another locking slot 16. The first blocking board 10 is rotated down. The first blocking board 10 is released, and the first positioning shaft 60 and the second positioning shaft 70 are moved from the directing surface 261 and the guiding surface 161 to the receiving surface 263 and the locking surface 163 respectively. The first positioning shaft 60 is engaged in another latching slot 26, and the second positioning shaft 70 is engaged in another locking slot 16. A second distance h2 between the first blocking board 10 and the second blocking board 20 is determined, and the distance between the first blocking board 10 and the holding board 103 is changed. In the illustrated embodiment of FIG. 5, the second distance h2 is greater than the first distance h1. Therefore, the tested product can be tested in different distance between the holding board 103 and the first blocking board 10.

It is to be understood, however, that even though numerous characteristics and advantages have been set forth in the foregoing description of embodiments, together with details of the structures and functions of the embodiments, the disclosure is illustrative only and changes may be made in detail, especially in the matters of shape, size, and arrangement of parts within the principles of the disclosure to the full extent indicated by the broad general meaning of the terms in which the appended claims are expressed.

What is claimed is:

1. A drop test apparatus comprising:
    a frame, the frame comprises a base board and a holding board above the base board, and the holding board configured for hold a tested product;
    a first blocking board located between the base board and the holding board and defining a plurality of locking slots, and the first blocking board configured for catching the tested product when the tested product is dropped from the holding board;
    a second blocking board secured to the base board, and the second blocking board defining a plurality of latching slots;
    two first pivot poles, a first rotating end of each of the two first pivot poles rotatably secured to the first blocking board, and a second rotating end opposite to the first rotating end engaged in one of the plurality of latching slots; and
    two second pivot poles rotatably secured to the two first pivot poles, a first pivot end of each of the two second pivot poles rotatably secured to the second blocking board, and a second pivot end opposite to the first pivot end engaged in one of the plurality of locking slots;
    wherein a distance between the first blocking board and the second blocking board is adjusted when the second rotating end of each of the two first pivot poles is moved out from the one of the plurality of latching slots, and the second pivot end of each of the two second pivot poles is moved out from the one of the plurality of latching slots.

2. The drop test apparatus of claim 1, wherein a first positioning shaft is secured to the second rotating end of each of the two first pivot poles and engaged in the one of the plurality of latching slots, and a second positioning shaft is secured to the second pivot end of each of the two second pivot poles and engaged in the one of the plurality of locking slots.

3. The drop test apparatus of claim 2, wherein the first positioning shaft is substantially perpendicular to the two first pivot poles.

4. The drop test apparatus of claim 2, wherein the second positioning shaft is substantially perpendicular to the two second pivot poles.

5. The drop test apparatus of claim 1, wherein the holding board is substantially parallel to the base board, and the first blocking board is substantially parallel to the second blocking board.

6. The drop test apparatus of claim 1, wherein the extending directions of each of the plurality of locking slots and latching slots are substantially parallel to each other and perpendicular to an rotating axis, and about which the first blocking board is rotated relative to each of the two first pivot poles.

7. The drop test apparatus of claim 1, wherein each of the plurality of locking slots comprises a guiding surface and a locking surface extending from the guiding surface, and the second pivot end of each of the two second pivot poles is moveable from the guiding surface to the locking surface to engage in the each of the plurality of locking slots.

8. The drop test apparatus of claim 7, wherein the guiding surface of each of the plurality of locking slots is slanted relative a bottom surface of the first blocking board, and the locking surface thereof is arc-shaped.

9. The drop test apparatus of claim 1, wherein each of the plurality of latching slots comprises a directing surface and a receiving surface extending from the directing surface, and the first rotating end of each of the two first pivot poles is moveable from the directing surface to the receiving surface to engage in the each of the plurality of latching slots.

10. The drop test apparatus of claim 9, wherein the directing surface of each of the plurality of latching slots is slanted relative a bottom surface of the second blocking board, and the receiving surface thereof is arc-shaped.

11. A drop test apparatus comprising:
    a frame, the frame comprising a base board and a holding board above the base board, and the holding board configured for hold a tested product;
    a first blocking board located between the base board and the holding board and configured for placing the tested product when the tested product is dropped from the holding board;
    a second blocking board secured to the base board;
    a first pivot pole, a first rotating end of the first pivot pole rotatably secured to the first blocking board, and a second rotating end opposite to the first rotating end supported on the second blocking board; and
    a second pivot pole rotatably secured to the first pivot pole, an angle defined between the first pivot pole and the second pivot pole, a first pivot end of each of the second pivot pole rotatably secured to the second blocking board, and a second pivot end opposite to the first pivot end supported on the first blocking board;

wherein a distance between the first blocking board and the second blocking board is adjusted when the angle is changed.

12. The drop test apparatus of claim 11, wherein the first blocking board defines a plurality of locking slots, the second blocking board defines a plurality of latching slots, the second rotating end of the first pivot pole is engaged in one of the plurality of latching slots, and the second pivot end of the second pivot pole is engaged in one of the plurality of locking slots.

13. The drop test apparatus of claim 12, wherein a first positioning shaft is secured to the second rotating end of the first pivot pole and engaged in the one of the plurality of latching slots, and a second positioning shaft is secured to the second pivot end of the second pivot pole and engaged in the one of the plurality of locking slots.

14. The drop test apparatus of claim 13, wherein the first positioning shaft is substantially perpendicular to the first pivot pole.

15. The drop test apparatus of claim 13, wherein the second positioning shaft is substantially perpendicular to the second pivot pole.

16. The drop test apparatus of claim 11, wherein the holding board is substantially parallel to the base board, and the first blocking board is substantially parallel to the second blocking board.

17. The drop test apparatus of claim 12, wherein the extending directions of each of the plurality of locking slots and latching slots are substantially parallel to each other and perpendicular to an rotating axis, about which the first blocking board is rotated relative to the first pivot pole.

18. The drop test apparatus of claim 12, wherein each of the plurality of locking slots comprises a guiding surface and a locking surface extending from the guiding surface, and the second pivot end of the second pivot pole is moveable from the guiding surface to the locking surface to engage in the each of the plurality of locking slots.

19. The drop test apparatus of claim 18, wherein the guiding surface of each of the plurality of locking slots is slanted relative a bottom surface of the first blocking board, and the locking surface thereof is arc-shaped.

20. The drop test apparatus of claim 12, wherein each of the plurality of latching slots comprises a directing surface and a receiving surface extending from the directing surface, and the second rotating end of the first pivot pole is moveable from the directing surface to the receiving surface to engage in the each of the plurality of latching slots.

* * * * *